(12) United States Patent
Suzuki

(10) Patent No.: US 12,099,030 B2
(45) Date of Patent: Sep. 24, 2024

(54) CARBON DIOXIDE GAS SENSOR

(71) Applicant: FUJI ELECTRIC CO., LTD., Kawasaki (JP)

(72) Inventor: Takuya Suzuki, Hachioji (JP)

(73) Assignee: FUJI ELECTRIC CO., LTD., Kawasaki (JP)

( * ) Notice: Subject to any disclaimer, the term of this patent is extended or adjusted under 35 U.S.C. 154(b) by 319 days.

(21) Appl. No.: 16/917,186

(22) Filed: Jun. 30, 2020

(65) Prior Publication Data
US 2020/0400606 A1   Dec. 24, 2020

Related U.S. Application Data

(63) Continuation of application No. PCT/JP2019/023607, filed on Jun. 14, 2019.

(30) Foreign Application Priority Data

Jul. 13, 2018   (JP) ................. 2018-133277

(51) Int. Cl.
*G01N 27/407*   (2006.01)
*C01F 17/247*   (2020.01)
(Continued)

(52) U.S. Cl.
CPC ....... *G01N 27/4074* (2013.01); *C01F 17/247* (2020.01); *G01N 27/14* (2013.01);
(Continued)

(58) Field of Classification Search
CPC .............. G01N 27/4074; G01N 27/14; G01N 27/4067; G01N 27/416; G01N 33/004;
(Continued)

(56) References Cited

U.S. PATENT DOCUMENTS

| 2004/0161474 | A1 | 8/2004 | Moerck et al. |
| 2009/0145220 | A1* | 6/2009 | Langenbacher ..... G01N 27/227 73/335.04 |
| 2014/0161885 | A1 | 6/2014 | Gore et al. |

FOREIGN PATENT DOCUMENTS

| CN | 103037870 A | 4/2013 |
| CN | 104129810 A | 11/2014 |

(Continued)

OTHER PUBLICATIONS

Chen et al. (G Chen et al., Lanthanum dioxide carbonate La2O2CO3 nanorods as a sensing material for chemoresistive CO gas sensor, Electrochemica Acta 127 (2014) 355-361). (Year: 2014).*

(Continued)

*Primary Examiner* — Luan V Van
*Assistant Examiner* — Shizhi Qian

(57) ABSTRACT

A gas sensor capable of detecting carbon dioxide and having high stability is provided. A carbon dioxide gas sensor comprising an insulating substrate 3 and a gas sensing layer 1 formed on one major surface of the insulating substrate 3 via electrodes 2, wherein the gas sensing layer 1 comprises:
(a) one or more rare earth metal oxycarbonates represented by $Ln_2O_2CO_3$, Ln being at least one rare earth metal element selected from Sc, Y, La, Ce, Nd, Sm, Eu, Gd, Tb, Dy, Ho, Er, Tm, Pr, Yb and Lu, the rare earth metal oxycarbonate containing a hexagonal rare earth metal oxycarbonate as a main component; or
(b) monoclinic samarium dioxycarbonate,
a production method of the gas sensor, and a method of selectively producing crystal polymorphism of lanthanum dioxycarbonate represented by $La_2O_2CO_3$ are provided.

3 Claims, 10 Drawing Sheets

(51) Int. Cl.
  *G01N 27/14* (2006.01)
  *G01N 27/406* (2006.01)
  *G01N 27/416* (2006.01)
(52) U.S. Cl.
  CPC ....... *G01N 27/4067* (2013.01); *G01N 27/416* (2013.01); *C01P 2002/60* (2013.01); *C01P 2004/61* (2013.01)
(58) Field of Classification Search
  CPC ... G01N 27/125; C01F 17/247; C01F 17/224; C01F 17/229; C01P 2002/60; C01P 2004/61
  See application file for complete search history.

(56) References Cited

FOREIGN PATENT DOCUMENTS

| CN | 106501448 | A |   | 3/2017 |   |
|---|---|---|---|---|---|
| EP |   2910940 | A1 | * | 8/2015 | ........... G01N 27/127 |
| JP | 2004205408 | A |   | 7/2004 |   |
| JP | 2006514600 | A |   | 5/2006 |   |
| JP | 2013531598 | A |   | 8/2013 |   |
| WO | 2004016553 | A2 |   | 2/2004 |   |
| WO | 2011143475 | A1 |   | 11/2011 |   |

OTHER PUBLICATIONS

Haensch et al. (A Haensch et al., Faster response times of rare-earth oxycarbonate based CO2 sensors and another readout strategy for real-world applications, Procedia Engineering 25 (2011) 1429-1432) (Year: 2011).*
Watanabe et al. (Y Watanabe et al., Dissociation pressure of lanthanum dioxide carbonate, J. Materials Science Letters 5 (1986) 135-136). (Year: 1986).*
Kodu et al. (Margus Kodu et al., Structure-dependent CO2 gas sensitivity of La2O2CO3 thin films, Hindawi Journal of Sensors 2017, pp. 1-6, cited in IDS) (Year: 2017).*
Guo et al. (Hiuming Guo et al., Growth of nanoporous high-entropy oxide thin films by pulsed laser deposition, Journal of Materials Research, 2022, 124-135) (Year: 2022).*
Guang et al. (Zhang Guang et al., Kinetics of thermal decomposition of lanthanum oxalate hydrate, Trans. Nonferrous Met. Soc. China 22 (2012) 925-934). (Year: 2012).*
Verma et al.,Multifunctional application of cytosine for the synthesis of hybrid homogenized nano-sized rare earth oxide (Re2O3) and rare earth oxycarbonate (Re2O2CO3) (Re=Nd, Sm) advance material via microwave irradiation, Protection of metals and physical chemistry of surfaces, 2017, 53(3), 444-451 (Year: 2017).*
Djerdj et al., Neodymium Dioxide Carbonate as a Sensing Layer for Chemoresistive CO2 Sensing, Chem. Mater., 2009, p. 5375-5381.
Kodu et al., Structure-Dependent CO2 Gas Sensitivity of La2O2CO3 Thin Films, Journal of Sensors, vol. 2017, https://doi.org/10.1155/2017/9591081.
Hirsch et al., High-energy resolution X-ray absorption and emission spectroscopy reveals insight into unique selectivity of La-based nanoparticles for CO2, PNAS, vol. 112, No. 52, Dec. 2012.
Chen et al., Lanthanum Dioxide Carbonate La2O2CO3 Nanorods as a Sensing Material for Chemoresistive CO2 Gas Sensor, Electrochimica Acta, Feb. 2014, p. 355-361.
Turcotte et al., On the Rare Earth Dioxymonocarbonates and Their Decomposition, Inorganic Chemistry, Aug. 2014, p. 238-246.
Artini et al., Phase stability study of the psuedobinary system Gd2O2CO3—Nd2O2CO3 (420° C. < T < 850° C., P=1 atm. CO2), J Therm Anal Calorim, (2013) 112, p. 499-503.
Haensch et al., Rare earth oxycarbonates as a material class for chemoresistive CO2 gas sensors, Procedia Engineering, Sep. 2012, p. 139-142.
Suzuki et al., Crystal Structure and CO2 Sensing Properties of Rare-earth oxycarbonates, 17th International Meeting on Chemical Sensors—IMCS 2018, p. 541-542.
International Search Report dated Sep. 17, 2019, in corresponding International Patent Application No. PCT/JP2019/023607 (2 pages).
Written Opinion of the International Searching Authority dated Sep. 17, 2019, in corresponding International Patent Application No. PCT/JP2019/023607 (4 pages).
Olafsen Anja et al: "Synthesis of rare earth oxide carbonates and thermal stability of Nd2O2C03 II", Journal of Materials Chemistry, GB, vol. 9, No. 10, Oct. 1999 (Oct. 1999), pp. 2697-2702, XP055823760.
Supplementary European Search Report for Application No. EP 19 83 3299 dated Jul. 26, 2021.
Hirsch et al., High-energy resolution X-ray absorption and emission spectroscopy reveals insight into unique selectivity of La-based nanoparticles for CO2, PNAS, vol. 112, No. 52, Dec. 2015.
Turcotte et al., On the Rare Earth Dioxymonocarbonates and Their Decomposition, Inorganic Chemistry, Feb. 1969, p. 238-246.
Haensch et al., Rare earth oxycarbonates as a material class for chemoresistive CO2 gas sensors, Procedia Engineering, Sep. 2010, p. 139-142.
Haensch et al., "CO$_2$ sensing with chemoresistive Nd$_2$O$_2$ CO$_3$ sensors—Operando insights", Procedia Chemistry, Elsevier, Amsterdam, NL, Sep. 1, 2009, pp. 650-653.
Ding et al., "Facile synthesis of La$_2$O$_2$CO$_3$ nanoparticle films and Its CO$_2$ sensing properties and mechanisms", Applied Surface Science, Elsevier, Amsterdam, NL| vol. 426, Jul. 22, 2017, pp. 725-733.
Supplementary Partial European Search Report dated Mar. 17, 2021, in corresponding European Patent Application No. 19833299.1.
Chinese Office Action dated Sep. 15, 2022 for Chinese Application No. 201980007178.X, 27 pages.
Zipeng Wei, "Controllable Synthesis of Hierarchical Porous Micro/Nano Materials with Multi-Shell Hollow Structures and Their Structure-Activity Relationships", Engineering Science and Technology I, No. 2, 2018.

* cited by examiner

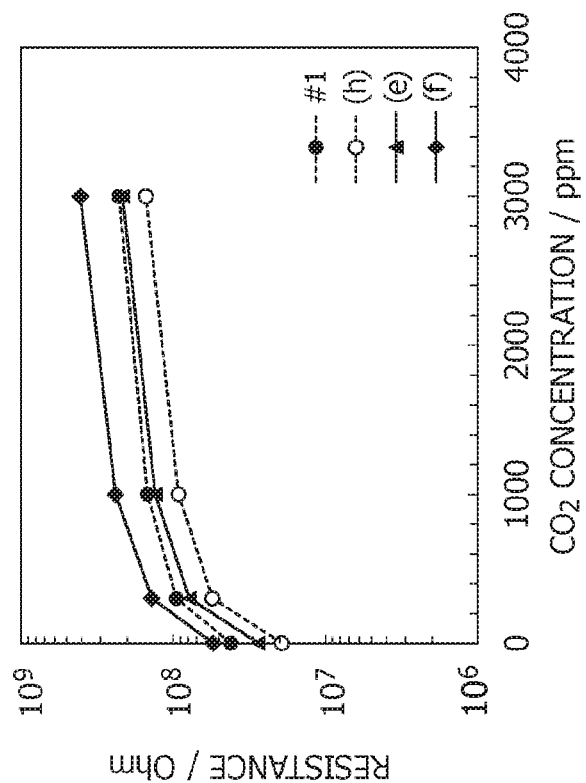
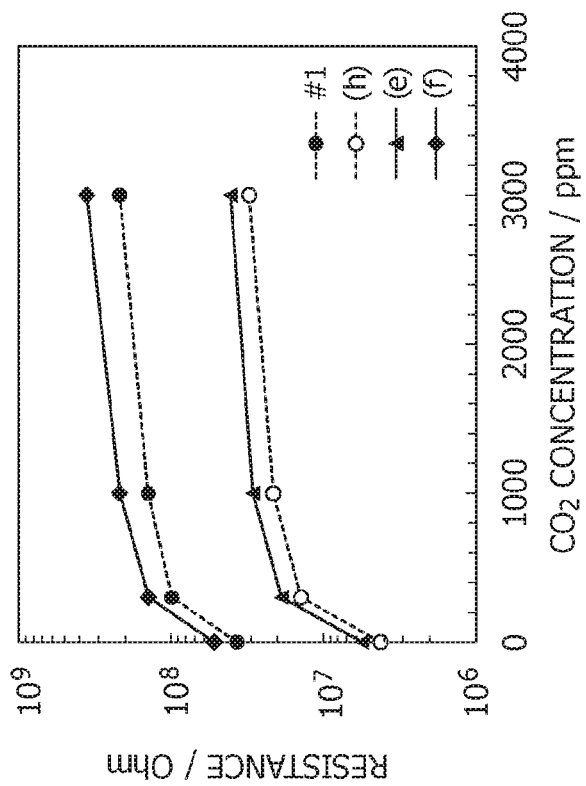
FIG.4A
FIG.4B

CARBON DIOXIDE GAS SENSOR

CROSS-REFERENCE TO RELATED APPLICATIONS

This application is a Continuation Application which claims the benefit under 35 U.S.C. § 111 of International Patent Application No. PCT/JP2019/023607 filed on Jun. 14, 2019, which claims foreign priority benefit under 35 U.S.C. § 119 of Japanese Patent Application No. 2018-133277 filed on Jul. 13, 2018, in the Japanese Intellectual Property Office, the contents of all of which are incorporated herein by reference.

TECHNICAL FIELD

The present invention relates to a carbon dioxide gas sensor, to a production method and aging method for a gas sensor, and to a production method for a rare earth oxycarbonate which can be used for a sensing layer of a gas sensor.

BACKGROUND ART

Detection of carbon dioxide gas (hereinafter, also referred to as $CO_2$ gas) is attracting attention not only in the field of environmental safety, such as in management of buildings and parking places, but also in the fields of agriculture and in food-related industries. In a current standard technology, detection of $CO_2$ gas is conducted using a nondispersive infrared (NDIR) $CO_2$ gas sensor. However, NDIRs are expensive and bulky, and thus, there are problems in that they are difficult to install. Therefore, a high-performance, low-cost, chemoresistive $CO_2$ gas sensor having a simple structure has been desired.

As a promising chemoresistive material that could be used for a $CO_2$ gas sensor, rare earth metal oxycarbonate (rare earth oxycarbonate) has been proposed (for example, see Non-Patent Literatures 1 to 4). Although there are families of rare earth metal oxycarbonates having different rare earth metals and different crystal polymorphisms, it is reported that lanthanum dioxycarbonate ($La_2O_2CO_3$) having monoclinic crystal structure is the most suitable material for a $CO_2$ gas sensor (Non-Patent Literature 2).

As a production method for a rare earth metal oxycarbonate, a method using a hydroxide of a rare earth metal ($Ln(OH)_3$) as a starting material is generally known (Non-Patent Literatures 2 to 4). Furthermore, synthesis of a rare earth metal oxycarbonate from a rare earth metal oxalate (rare earth oxalate) is also known (Non-Patent Literature 5). It has been reported that $Gd_2O_2CO_3$—$Nd_2O_2CO_3$ pseudobinary system, which functions as a luminous body, can be produced by thermally decomposing an oxalate hydrate represented by $Gd_{2-x}Nd_x[C_2O_4]_3 \cdot nH_2O$ under conditions of 420 to 850° C. and 1 atm for 3 weeks (Non-Patent Literature 6). However, it has not been reported that this pseudobinary system may function as a gas sensor.

A solid electrolyte type carbon dioxide gas sensor element, in which a working electrode layer including an oxycarbonate of a rare earth element and a zeolite is formed on the surface of the solid electrolyte layer, is also known (Patent Literature 1).

REFERENCE DOCUMENT LIST

Patent Document

Patent Literature 1: Japanese Patent Application Laid-Open No. 2004-205408

Non-Patent Documents

Non-Patent Literature 1: Chem. Mater. 21 (2009) 5375-5381
Non-Patent Literature 2: Journal of Sensors, Volume 2017, Article ID 9591081, 6 pages
Non-Patent Literature 3: PNAS Dec. 29, 2015. 112 (52) 15803-15808
Non-Patent Literature 4: Electrochimica Acta 127 (2014) 355-361
Non-Patent Literature 5: Inorg. Chem., 1969, 8 (2), 238-246
Non-Patent Literature 6: J Therm Anal Calorim (2013) 112:499-503

SUMMARY OF THE INVENTION

Problem to be Solved by the Invention

A chemoresistive gas sensing layer material having higher performance, a production method therefor, and a gas sensor therewith are desired for practical application as a thin film gas sensor.

Means for Solving the Problem

The inventors investigated a production method for a rare earth metal oxycarbonate as a chemoresistive material, and as a result, the inventors discovered the material suitable for a gas sensing layer of a $CO_2$ gas sensor and a production method of $CO_2$ gas sensor, and finally completed the present invention.

According to one embodiment, the present invention relates to a carbon dioxide gas sensor comprising an insulating substrate and a gas sensing layer formed on one major surface of the insulating substrate via electrodes, wherein the gas sensing layer comprises:

(a) one or more rare earth metal oxycarbonates represented by $Ln_2O_2CO_3$, Ln being at least one rare earth metal element selected from Sc, Y, La, Ce, Nd, Sm, Eu, Gd, Tb, Dy, Ho, Er, Tm, Pr, Yb and Lu, the rare earth metal oxycarbonate containing a hexagonal rare earth metal oxycarbonate as a main component; or (b) monoclinic samarium dioxycarbonate.

In the above gas sensor, the gas sensing layer preferably comprises hexagonal lanthanum dioxycarbonate or monoclinic samarium dioxycarbonate.

According to another embodiment, the present invention relates to a method for production of a carbon dioxide gas sensor comprising steps of production of a sensor structure comprising an insulating substrate and a gas sensing layer formed on one major surface of the insulating substrate via electrodes, the gas sensing layer comprising one or more rare earth metal oxycarbonates represented by $Ln_2O_2CO_3$, Ln being at least one rare earth metal element selected from Sc, Y, La, Ce, Nd, Sm, Eu, Gd, Tb, Dy, Ho, Er, Tm, Pr, Yb and Lu; and aging the sensor structure, wherein the aging comprises a step of continuously operating the sensor structure for 48 hours or more in a gas atmosphere containing 300 to 3000 ppm of carbon dioxide and having humidity of 20% to 90% under the condition of heating the gas sensing layer to 300 to 400° C.

In the step of production of the sensor structure in the method for production of the carbon dioxide gas sensor, the rare earth metal oxycarbonate preferably comprises monoclinic rare earth metal oxycarbonate.

According to another embodiment, the present invention relates to a method for production of a carbon dioxide gas sensor comprising a step of production of a sensor structure comprising an insulating substrate and a gas sensing layer formed on one major surface of the insulating substrate via electrodes, the gas sensing layer comprising monoclinic samarium dioxycarbonate.

According to yet another embodiment, the present invention relates to a method for aging a carbon dioxide gas sensor, comprising a step of continuously operating a carbon dioxide gas sensor comprising an insulating substrate and a gas sensing layer formed on one major surface of the insulating substrate via electrodes, wherein the gas sensing layer comprises one or more rare earth metal oxycarbonates represented by $Ln_2O_2CO_3$, Ln being at least one rare earth metal element selected from Sc, Y, La, Ce, Nd, Sm, Eu, Gd, Tb, Dy, Ho, Er, Tm, Pr, Yb and Lu, for 48 hours or more in a gas atmosphere containing 300 to 3000 ppm of carbon dioxide and having a humidity of 20% to 90% under the conditions of heating the gas sensing layer to 300 to 400° C.

According to yet another embodiment, the present invention relates to a method for producing one or more rare earth metal oxycarbonate represented by $Ln_2O_2CO_3$, Ln being at least one rare earth metal element selected from Sc, Y, La, Ce, Nd, Sm, Eu, Gd, Tb, Dy, Ho, Er, Tm, Pr, Yb and Lu, comprising a step of heating a rare earth metal carboxylate or rare earth metal carbonate, or a hydrate thereof at 425 to 575° C. for 2 to 80 hours.

According to yet another embodiment, the present invention relates to a method for selectively producing crystal polymorphism in lanthanum dioxycarbonate, represented by $La_2O_2CO_3$, comprising a step of heating lanthanum acetate hydrate represented by $La[CH_3COO]_3 \cdot nH_2O$ or lanthanum oxalate hydrate represented by $La_2[C_2O_4]_3 \cdot nH_2O$ at a heating temperature of 425 to 575° C. for 2 to 80 hours in a gas atmosphere containing 350 to 500 ppm of carbon dioxide, wherein monoclinic lanthanum oxycarbonate, hexagonal lanthanum oxycarbonate, and lanthanum oxycarbonate containing both are selectively produced by adjusting the heating temperature and the heating time.

The method for selectively producing crystal polymorphism in the lanthanum dioxycarbonate preferably comprises:

(a) a step of obtaining monoclinic lanthanum dioxycarbonate by heating at 525 to 575° C. for 5 to 8 hours, or by a step of heating at 475 to 525° C. for 6 to 20 hours or by a step of heating at 425 to 475° C. for 2 to 80 hours, (b) a step of obtaining lanthanum dioxycarbonate containing both monoclinic and hexagonal crystal structures by heating at 525 to 575° C. for 15 to 20 hours, or (c) a step of obtaining hexagonal lanthanum dioxycarbonate by heating at 475 to 575° C. for 60 to 80 hours.

According to yet another embodiment, the present invention relates to a method for selectively producing monoclinic samarium dioxycarbonate represented by $Sm_2O_2CO_3$, comprising a step of heating samarium acetate hydrate represented by $Sm[CH_3COO]_3 \cdot nH_2O$ or samarium oxalate hydrate represented by $Sm_2[C_2O_4]_3 \cdot nH_2O$ at a heating temperature of 425 to 475° C. for 2 to 80 hours in a gas atmosphere containing 350 to 500 ppm of carbon dioxide.

Effects of the Invention

According to the present invention, a small-sized chemoresistive $CO_2$ gas sensor having high performance, which comprises a gas sensing layer containing hexagonal rare earth metal oxycarbonate or monoclinic samarium dioxycarbonate having high stability as a main component of rare earth metal oxycarbonate, can be obtained. Furthermore, crystal polymorphism in lanthanum oxycarbonate and monoclinic samarium dioxycarbonate, which may be used for a gas sensing layer, can be selectively produced.

BRIEF DESCRIPTION OF THE DRAWINGS

FIG. 4A to 4B are graphs showing the results of evaluating $CO_2$ sensitivity property (resistance values) before and after the durability test for the gas sensors comprising lanthanum dioxycarbonate used for the gas sensing layer. FIG. 4A is a graph showing $CO_2$ sensitivity property (resistance values) before the durability test, and FIG. 4B is a graph showing $CO_2$ sensitivity property (resistance values) after the durability test.

FIG. 5A, FIG. 5B and FIG. 5C are graphs showing results of evaluating the $CO_2$ gas sensor signal ($R_g/R_0$), sensitivity ($\alpha$) and changes of sensor resistance values (after durability test/initial stage), respectively.

FIG. 6A is a graph showing change of sensor resistance values with respect to aging treatment time and aging treatment condition, FIG. 6B is a graph showing ratios of hexagonal lanthanum dioxycarbonate (mass %) with respect to aging treatment time and treatment condition.

FIG. 11A, FIG. 11B and FIG. 11C are graphs showing results of evaluating the $CO_2$ gas sensor signal ($R_g/R_0$) in an atmosphere containing 1000 ppm of $CO_2$, sensitivity ($\alpha$), and changes of sensor resistance values (after durability test/initial stage) in an atmosphere containing 1000 ppm of $CO_2$, respectively.

FIG. 12A and FIG. 12B show test results of gas sensing layers composed of hexagonal lanthanum dioxycarbonate and monoclinic samarium dioxycarbonate, respectively.

FIG. 13A and FIG. 13B show test results of gas sensing layers composed of hexagonal lanthanum dioxycarbonate and monoclinic samarium dioxycarbonate, respectively.

MODE FOR CARRYING OUT THE INVENTION

Hereinafter, the embodiments of the present invention will be described with reference to the drawings. However, the present invention is not limited to the embodiments described below.

First Embodiment: Gas Sensor

Figure 1:
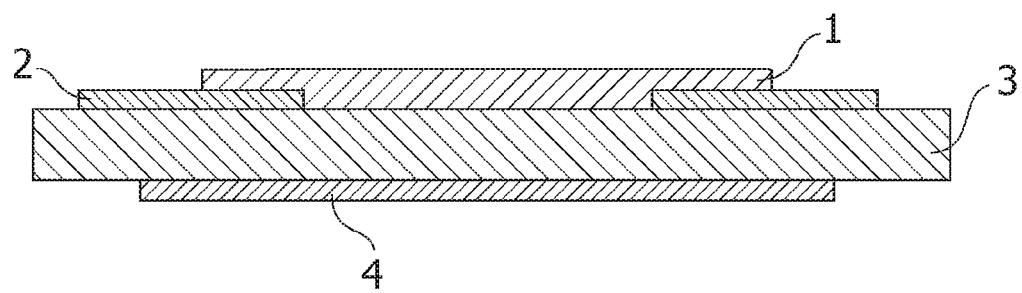
FIG. 1 is a schematic view showing a cross-sectional structure of the gas sensor according to one aspect in an embodiment of the present invention.

According to the First Embodiment, the present invention relates to a $CO_2$ gas sensor. FIG. 1 is a schematic cross-sectional view showing one example of the gas sensor according to the first aspect of the present embodiment. Referring to FIG. 1, the gas sensor 1 mainly comprises the gas sensing layer 1, electrodes 2, insulating substrate 3, and heating layer 4. FIG. 1 schematically shows a configuration of the gas sensor. The size and thickness of each part are not exact, and relative relationships of position and size are not limited to the aspect shown in the figure.

The insulating substrate 3 may be any substrate as long as it can ensure electrical insulation between the heating layer 4 and the electrodes 2. For example, a silicon substrate with the oxide film and an alumina substrate can be used, but the insulating substrate 3 is not limited thereto. The heating layer 4 is provided on one major surface of the insulating substrate 3. The heating layer 4 may be any layer as long as it can heat gas sensing layer 1 to a predetermined operating temperature through the insulating substrate 3. Pt film etc. can be used as the heating layer, but the heating layer 4 is not limited thereto. In the illustrated aspect, a gas sensor provided with a heating layer is exemplified; however, a heating layer may not be an essential constituent of the gas sensor of the present invention. A heating layer or an alternative heating device will be described below.

The electrodes 2 are provided on the major surface of the insulating substrate 3 opposite to the heating layer 4. The electrodes 2 are preferably a platinum (Pt) film or a gold (Au) film, and usually, comb teeth-shaped electrodes can be used.

The gas sensing layer 1 is provided on a major surface of the insulating substrate 3 so as to cover the electrodes 2. The gas sensing layer 1 comprises a chemoresistive material, and may optionally comprises an inorganic binder, aggregate, conductive material etc. In the present invention, the chemoresistive material is a rare earth metal oxycarbonate. The rare earth metal oxycarbonate is preferably one or more rare earth metal oxycarbonate represented by $Ln_2O_2CO_3$. In the chemical formula, Ln is one or more rare earth metal elements selected form Sc (scandium), Y (yttrium), La (lanthanum), Ce (cerium), Nd (neodymium), Sm (samarium), Eu (europium), Gd (gadolinium), Tb (terbium), Dy (dysprosium), Ho (holmium), Er (erbium), Tm (thulium), Pr (praseodymium), Yb (ytterbium) and Lu (lutetium). The rare earth metal oxycarbonate may be a composite metal salt, and may comprise two or more metals selected from the above in any proportion. Among these, lanthanum dioxycarbonate, samarium dioxycarbonate or gadolinium dioxycarbonate are particularly preferable in terms of sensitivity and stability.

In an aspect of the present invention, a main component of the rare earth metal oxycarbonate as a chemoresistive material may be hexagonal rare earth metal oxycarbonate. "A main component of the rare earth metal oxycarbonate is hexagonal rare earth metal oxycarbonate" means that at least 95% of the rare earth metal oxycarbonate has hexagonal crystal structure, preferably the rare earth metal oxycarbonate is substantially composed of hexagonal crystal structure, and further preferably 100% of the rare earth metal oxycarbonate has hexagonal crystal structure. The reason is that a monoclinic crystal structure is unstable and tends to transform into a hexagonal crystal structure, and thus, a resistance value of the sensor may change in association with the transformation of the structure. The content (%) of the rare earth oxycarbonate having a specific crystal structure in the rare earth metal oxycarbonate can be calculated by measuring the ratio of peaks using an X-ray diffractometer.

In another aspect of the present invention, a main component of the rare earth metal oxycarbonate as a chemoresistive material may be monoclinic samarium dioxycarbonate. The definition of a main component is similar to that described above.

Examples of an optional component of the gas sensing layer 1 include a binder and an aggregate for maintaining mechanical strength of the gas sensing layer 1. As a binder and an aggregate, those which are usually used can be used within a range not inhibiting chemoresistivity of the rare earth oxycarbonate, and for example, inorganic binders such as alumina sol can be exemplified, but they are not limited to a particular material. Examples of other optional components include a conductive material for adjusting the resistivity of the gas sensing layer 1. These optional components may be included in amount of 20 mass % or less, preferably 15 mass % or less, relative to the total mass of the gas sensing layer 1.

The heating layer 4 of the gas sensor is electrically connected to a driving processor, which is not shown, and the driving processor drives the heating layer 4. The gas sensing layer 1 is electrically connected to the driving processor, which is also not shown, via the electrodes 2 of the gas sensor, and the driving processor can read an electrical resistance value (referred to a sensor resistance value) of gas sensing layer 1. In the present embodiment, as a heating device for heating the gas sensing layer to a predetermined temperature, the heating layer provided on the side of the insulating substrate opposite to the gas sensing layer is illustrated; however, in the present invention, the shape of the heating device is not limited to a heating layer, and the arrangement of the heating device is also not limited to the aspect shown in the figure. In one embodiment, the heating device may be provided on the same surface of the insulating substrate as the gas sensing layer with the heating device being separated from the gas sensing layer. In another embodiment, the heating device may be provided on the major surface of the insulating substrate opposite to the surface on which the gas sensing layer is provided, and the heating device may be provided so as to be partially or completely embedded. In another embodiment, the heating device may be provided according to an aspect in which the heating device does not come into contact with the stack of the insulating substrate and the gas sensing layer, and for example, the heating device may be provided in a housing which contains the insulating substrate and the gas sensing layer. In all cases, the heating device may be a heating layer or a heater which is not in the form of a layer, and may include one or more heating devices, as long as the heating device can heat the gas sensing layer to a predetermined temperature.

Next, the gas sensor according to the present embodiment will be described with reference to the production method. The production method of the gas sensor according to the present embodiment comprises a step of production of the sensor structure comprising the insulating substrate 3, electrodes 2, gas sensing layer 1, and heating layer 4, and an optional step of aging the sensor structure.

(1) Step of Production of Sensor Structure

In the step of production of the sensor structure, the heating layer 4 is formed on one major surface of the insulating substrate 3, and the electrodes 2 are formed on the other major surface. Formation of the heating layer 4 and the electrodes 2 on the insulating substrate 3 can be conducted by a usually used method. The heating layer 4 and the electrodes 2 can be respectively connected to a driving processor, which is not shown, by the usually used method. As for a sensor structure provided with a heating device other than a heating layer, the heating device can be attached to a suitable place by a commonly used method and connected to a driving power source etc.

Formation of the gas sensing layer 1 comprises steps of preparing a rare earth metal oxycarbonate represented by $Ln_2O_2CO_3$ (Ln is the same as defined above) which is a main component of the gas sensing layer 1, and mixing the rare earth metal oxycarbonate and a solvent and, if needed, an optional component such as a binder, to form a film on the insulating substrate 3 on which the electrode 2 is formed.

The rare earth metal oxycarbonate prepared before film formation may contain a hexagonal rare earth metal oxycarbonate as a main component, and preferably may contain 100% of hexagonal rare earth metal oxycarbonate. When a film is formed using a rare earth metal oxycarbonate comprising 100% of hexagonal crystal structure, the aging step described below may not be necessary. Alternatively, rare earth metal oxycarbonate substantially composed of only monoclinic crystal structure, or rare earth metal oxycarbonate containing both monoclinic and hexagonal crystal structures may be used as a material for the gas sensing layer 1. Also in the case in which a film is formed using the rare earth metal oxycarbonate containing monoclinic crystal structure as a raw material, the gas sensing layer 1 in which a main component of the rare earth metal oxycarbonate has hexagonal crystal structure, preferably the gas sensing layer 1 composed of 100% of hexagonal rare earth metal oxycarbonate, can be produced in the subsequent aging step. The production method and the conditions of selective production of crystal polymorphism of lanthanum dioxycarbonate, which is one example of rare earth metal oxycarbonates, will be described below. Depending on the production conditions of a rare earth metal oxycarbonate, carbon may be contained in the product; however, a product containing carbon is not preferable as a sensing layer material. The reason is that carbon is gradually removed by combustion by heat generated during operation of the sensor, and thus, change of sensor resistance values may be caused. Since the rare earth metal oxycarbonate containing carbon as an impurity turns black, it can be visually checked, or it can be confirmed whether carbon is contained or not by methods such as Electron Probe Micro Analyzer (EPMA) or Raman spectroscopy. The "carbon" as used herein does not refer to a carbon atom, but to a black colored carbon compound.

Alternatively, the rare earth metal oxycarbonate prepared before film formation may be monoclinic samarium dioxycarbonate.

In the step of mixing a rare earth metal oxycarbonate and a solvent, solvents which have high boiling point and lower volatility such as propane-1,2-diol, ethyl carbitol, diethylene glycol monoethyl ether and ethylene glycol can be used. The rare earth metal oxycarbonate and the solvent are mixed thoroughly to obtain a paste, then a film is formed by a screen printing method, drop coating method, spray coating method etc. at a desired thickness on the insulating substrate 3 on which the electrode 2 is formed. Then, the obtained film is dried at 60 to 80° C. for 10 to 15 hours. After drying, the film is preferably heat-treated for 10 to 15 minutes under the heat treatment conditions identical to those for production of the rare earth metal oxycarbonate. Thus, the sensor can be obtained in which the heating layer 4 can be driven and electrical resistance values of the gas sensing layer can be read by electrifying the sensor.

(2) Aging Step

The aging is an optional step, and it may not be conducted when a constituent of the sensing layer is monoclinic samarium dioxycarbonate. In the sensor structure obtained in the previous step, the rare earth metal oxycarbonate in the gas sensing layer 1 substantially retains the crystal structure before film formation. Therefore, in the case of production of the gas sensor having the sensing layer 1 containing hexagonal rare earth metal oxycarbonate as a main component, wherein monoclinic rare earth metal oxycarbonate (except for monoclinic samarium dioxycarbonate) is contained in the sensing layer before film formation, the subsequent aging step is conducted. The aging step can be conducted by continuously operating the sensor structure for 48 hours or more in a gas atmosphere containing 300 to 3000 ppm of carbon dioxide and having relative humidity of 20% to 90% at 20° C. under the condition of making the temperature of the gas sensing layer 300 to 400° C. The continuous operation time may be, for example, 3 days or more, or may be about 10 days or less, but it is not limited thereto. The aging condition varies depending on the content of monoclinic crystal structure in the film-formed gas sensing layer 1. For example, when the rare earth metal oxycarbonate of the gas sensing layer contains 100%, 80% and 20% of monoclinic crystal structure, the aging time may be about 7 days, about 6 days, and about 2 days, respectively. The aging step can be terminated at the time when substantially 100% of the rare earth metal oxycarbonate has been transformed into a hexagonal crystal structure, and thus, the required condition of aging treatment time can also be determined by a preliminary experiment using an Operando-XRD apparatus which enables real time analysis of crystal structure change. In the sensor comprising the gas sensing film-formed using a rare earth metal oxycarbonate as a raw material during film formation wherein the rare earth metal oxycarbonate contains hexagonal crystal structure as a main component, aging may be conducted or may not be conducted. Also in the case of production of the gas sensor having the sensing layer 1 containing monoclinic samarium dioxycarbonate as a main component, aging may be conducted.

When the gas sensor having the sensing layer 1 containing a hexagonal rare earth metal oxycarbonate as a main component is produced, substantially 100% of the rare earth metal oxycarbonate contained in the gas sensing layer 1 becomes a hexagonal crystal structure by conducting the above aging step, and thus, a gas sensor having excellent stability can be produced. The sensing layer 1 containing monoclinic samarium dioxycarbonate as a main component can serve as a gas sensor having excellent stability and sensitivity even without conducting the aging step. The gas sensor according to the present embodiment is useful as a detection sensor of carbon dioxide gas, and in particular, can selectively detect carbon dioxide gas while distinguishing it from various gases such as hydrogen gas, carbon monoxide gas, and ethanol. The inventors further discovered that in the sensor according to the present embodiment, the gas sensing layer, in which a main component of the rare earth metal oxycarbonate is hexagonal rare earth metal oxycarbonate, exhibits high sensitivity to two parameters, carbon dioxide concentration and humidity, at different temperatures. Therefore, when the gas sensor according to the present embodiment is operated at different temperatures which are inherent to carbon dioxide and humidity, respectively, and the respective resistance values are obtained, it is considered that dual sensing of carbon dioxide and humidity becomes possible.

Figure 2:
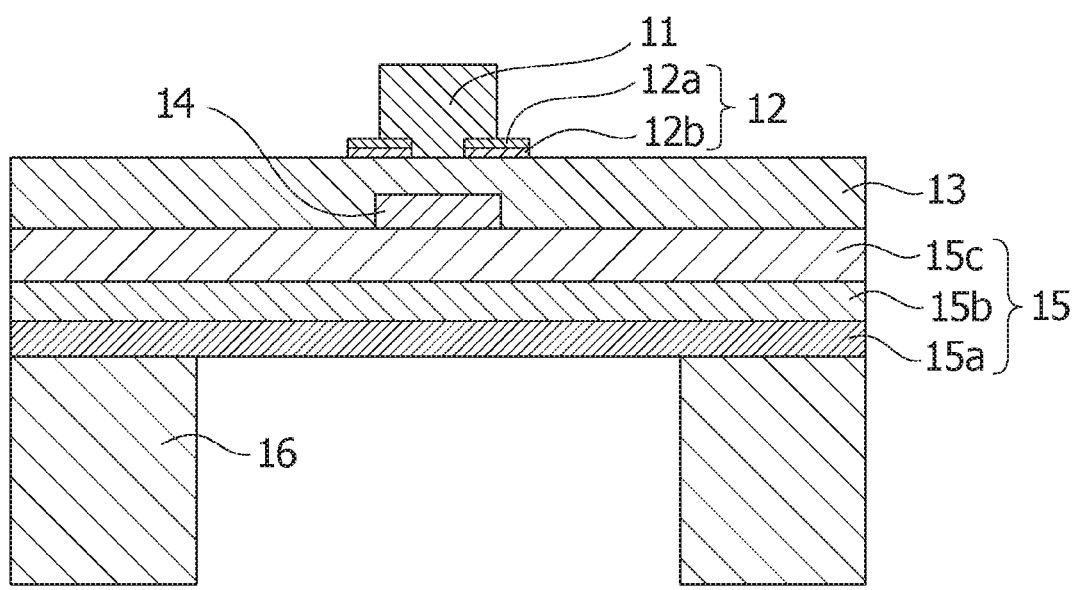
FIG. 2 is a schematic view showing a cross-sectional structure of the gas sensor according to another aspect of the present invention.

As another aspect of the gas sensor according to the present embodiment, a diaphragm-type thin film gas sensor may be mentioned. FIG. 2 schematically shows a cross-section of a diaphragm-type thin film gas sensor. The diaphragm-type gas sensor comprises silicon substrate (hereinafter referred to as Si substrate) 16, thermally insulating support layer 15, heating layer 14, insulating substrate 13, electrodes 12, gas sensing layer 11.

The Si substrate 16 is formed of silicon (Si), and through holes are formed on the Si substrate at the locations directly over which the gas sensing layer 11 is positioned. The thermally insulating support layer 15 covers the openings of the through holes to form a diaphragm, and is provided on the Si substrate 16. Specifically, the thermally insulating support layer 15 has a three-layer structure comprising thermally oxidized $SiO_2$ layer 15a, CVD-$Si_3N_4$ layer 15b and CVD-$SiO_2$ layer 15c. The thermally oxidized $SiO_2$ layer 15a is formed as a heat insulation layer, and has a function of reducing heat capacity by preventing heat generated in the heating layer 14 from being conducted to the side of the Si substrate 16. Furthermore, this thermally oxidized $SiO_2$ layer 15a has a high resistance to plasma etching, which facilitates formation of through holes on the Si substrate 16 by plasma etching. The CVD-$Si_3N_4$ layer 15b is formed on upper side of the thermally oxidized $SiO_2$ layer 15a. The CVD-$SiO_2$ layer 15c enhances adhesion to the heating layer 14, and in addition, ensures electrical insulation. The $SiO_2$ layer formed by CVD (chemical vapor deposition method) has a low internal stress.

The heating layer 14 may be a Pt—W film in the form of thin film, and is provided on the upper side of approximately the center of the thermally insulating support layer 15. Furthermore, the heating layer 14 is connected to a driving processor (not shown), and configured to be subjected to power feeding. The insulating substrate 13 may be a sputtered $SiO_2$ layer for ensuring electrical insulation, and is provided so as to cover the thermally insulating support layer 15 and the heating layer 14. The insulating substrate 13 can ensure electrical insulation between the heating layer 14 and the electrodes 12a. Furthermore, the insulating substrate 13 can enhance adhesion to the gas sensing layer 11.

The bonding layer 12b is, for example, Ta film (tantalum film) or Ti film (titanium film), and a left-and-right pair of the bonding layers 12b is provided on the insulating substrate 13. These bonding layers 12b are interposed between the electrodes 12a and the insulating substrate 13 to enhance bonding strength. The electrodes 12a are, for example, Pt film (platinum film) or Au film (gold film), and a left-and-right pair of the electrodes 12a is provided so as to serve as sensing electrodes of the gas sensing layer 11. The gas sensing layer 11 is formed astride a pair of the electrodes 12a on the insulating substrate 13 across. In particular, the composition of the gas sensing layer 11 is the same as described in the embodiment with reference to FIG. 1. Specifically, 100% of rare earth metal oxycarbonate is preferably hexagonal rare earth metal oxycarbonate. In another embodiment, a main component in the composition of gas sensing layer 11 is preferably monoclinic samarium dioxycarbonate.

Similarly to the sensor according to the first aspect, the heating layer 14 of the gas sensor is electrically connected to a driving processor (not shown in the figures), and the driving processor drives the heating layer 14. Furthermore, the gas sensing layer 11 is electrically connected to the driving processor which is also not shown via the electrodes 12a of the gas sensor so that the driving processor can read electrical resistance values of the gas sensing layer 11.

A diaphragm-type gas sensor can also be produced by production of the gas sensor structure shown in FIG. 2 by a usual method, and then, if necessary, conducting aging under similar conditions to those of the sensor shown in FIG. 1. The relationship between the material used for film formation and the aging condition is the same as described for the sensor shown in FIG. 1.

Such gas sensors having a diaphragm structure may provide high thermal insulation and low heat capacity. Furthermore, in the gas sensor, heat capacity of each constituent of electrodes 12a, gas sensing layer 11, and heating layer 14 can be reduced by techniques such as MEMS (micro-electrical-mechanical system). Therefore, temperature change with time is greater during operation of the heater, and thus, thermodesorption can be achieved in an extremely short time.

In the present embodiment, the gas sensor is described by showing specific examples of structures of the sensors in FIGS. 1 and 2; however, the present invention is not limited thereto, and the gas sensor may have any structure as long as the sensor comprises the structure in which the gas sensing layer is driven to a predetermined temperature by a heating device and electrical resistance values of the gas sensing layer can be read. When the gas sensing layer described in the present embodiment is used, a compact high-performance $CO_2$ gas sensor having high stability can be provided.

Second Embodiment: Production Method of Rare Earth Metal Oxycarbonate

According to the second embodiment, the present invention relates to a production method for a rare earth metal oxycarbonate. The production method for a rare earth metal oxycarbonate (Ln is the same as defined above) represented by $Ln_2O_2CO_3$, comprises a step of heating the rare earth metal carboxylate or the rare earth metal carbonate, or the hydrate thereof at 425 to 575° C. for 2 to 80 hours or 5 to 80 hours in a gas atmosphere.

Figure 3:
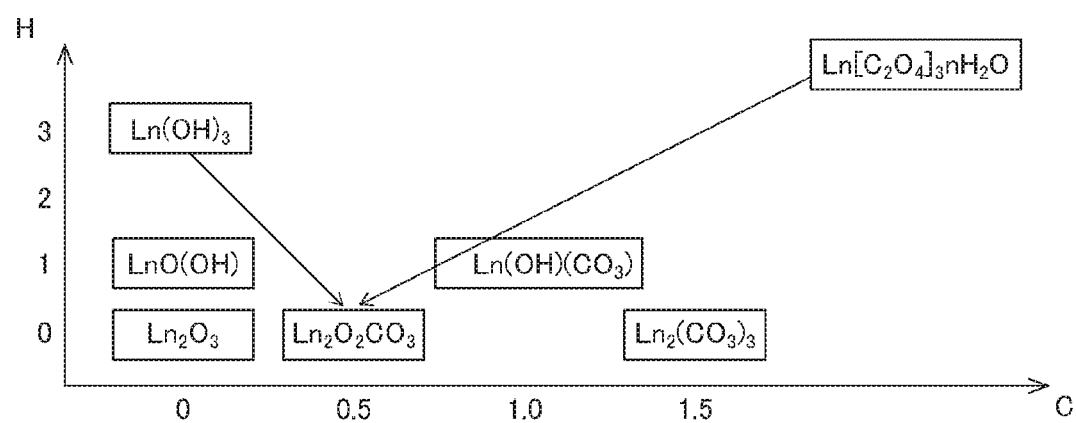
FIG. 3 is a diagram showing two different synthetic pathways of a rare earth metal oxycarbonate.

In the production method of the present embodiment, the rare earth metal carboxylate or a rare earth metal carbonate, or the hydrate thereof can be used as a starting material. As the rare earth metal constituting a rare earth metal carboxylate, those corresponding to Ln in the target rare earth metal oxycarbonate represented by $Ln_2O_2CO_3$ can be used, and the rare earth metal can be selected from Ln as defined above. Specific examples of rare earth metal carboxylates include, but are not limited to, oxalates represented by $Ln_2[C_2O_4]_3$ or oxalate hydrates represented by $Ln_2[C_2O_4]_3 \cdot nH_2O$, carbonates represented by $Ln_2[CO_3]_3$ or hydrate thereof, acetates represented by $Ln[CH_3COO]_3$ or hydrates thereof. Any organic acid salt of rare earth metal may be used, as long as carbon dioxide is generated by thermal decomposition of the salt at a specified temperature. FIG. 3 is a diagram showing pathways of synthesizing the rare earth metal oxycarbonate using $Ln_2[C_2O_4]_3 \cdot nH_2O$ which is an example of a rare earth metal carboxylate hydrate and a rare earth metal hydroxide, respectively, as starting materials. In the diagram, the horizontal axis C represents the number of carbon atoms per rare earth element Ln in the compound, and the vertical axis H represents the number of hydrogen atoms per rare earth element Ln in the compound. In the present invention, the synthetic pathway using not the rare earth metal hydroxide, but the rare earth metal carboxylate or the rare earth metal carbonate, or the hydrate thereof as a starting material, is adopted.

In a step of heating, the rare earth metal carboxylate or the rare earth metal carbonate, or the hydrate thereof which is in the form of solid powder in room temperature can be preferably placed in a heat resistant open-type alumina container and the like, and be heated in a heating furnace. The heating temperature is preferably 425 to 575° C., and preferably maintained at a constant temperature during heating. The heating time may be 2 to 80 hours or 5 to 80 hours. One example of the heating conditions may be a heating temperature of 475 to 575° C. and a heating time of 15 to 75 hours. Another example of the heating conditions may be a heating temperature of 475 to 525° C. and a heating time of 6 to 20 hours, or 15 to 20 hours. Yet another example of the heating condition may be a heating temperature of 475 to 575° C. and a heating time of 65 to 75 hours. The atmosphere during heating is not particularly limited, but it may be air, a closed system, or an atmosphere to which a gas such as air can be continuously supplied. One example of an atmosphere to which a gas such as air can be continuously supplied is an atmosphere to which a gas comprising 350 to 500 ppm of carbon dioxide and moisture of 20 to 80% relative humidity at 20° C. can be supplied. However, supplying of a gas comprising carbon dioxide and moisture is not essential. The reason is that a rare earth metal oxycarbonate can be produced by carbon dioxide generated during thermal decomposition of a rare earth metal carboxylate or a hydrate thereof.

Third Embodiment: Selective Production Method of Polymorph of Lanthanum Dioxycarbonate In production of a rare earth metal oxycarbonate, when the rare earth metal is lanthanum (La) and the starting material is lanthanum oxalate hydrate represented by $La_2[C_2O_4]_3 \cdot nH_2O$ or acetate hydrate represented by $La[CH_3COO]_3 \cdot nH_2O$, different crystal polymorphism can be selectively produced. Specifically, monoclinic crystal structure, hexagonal crystal structure, or a mixture thereof, can be separately produced by varying the conditions of temperature and time while the starting material and the production conditions are within the scope of the second embodiment.

Lanthanum dioxycarbonate composed of hexagonal crystal structure can be obtained by heating $La_2[C_2O_4]_3 \cdot nH_2O$ or $La[CH_3COO]_3 \cdot nH_2O$ at 475 to 575° C. for 60 to 80 hours. Lanthanum dioxycarbonate composed of monoclinic crystal structure can be obtained by heating $La_2[C_2O_4]_3 \cdot nH_2O$ or $La[CH_3COO]_3 \cdot nH_2O$ at 525 to 575° C. for 5 to 8 hours, or heating at 475 to 525° C. for 6 to 20 hours or 15 to 20 hours, or heating at 425 to 475° C. for 2 to 80 hours or 60 to 80 hours. Lanthanum dioxycarbonate containing both hexagonal and monoclinic crystal structures can be obtained by heating $La_2[C_2O_4]_3 \cdot nH_2O$ or $La[CH_3COO]_3 \cdot nH_2O$ at 525 to 575° C. for 15 to 20 hours.

According to the production method of the present embodiment, lanthanum dioxycarbonate containing specific crystal polymorphism can be selectively produced. Therefore, the selectively produced lanthanum dioxycarbonate composed of hexagonal crystal structure can be used as a material for film formation of the gas sensing layer of the first embodiment. Alternatively, lanthanum dioxycarbonate composed of monoclinic crystal structure or lanthanum dioxycarbonate containing both hexagonal and monoclinic crystal structure can also be used as a material for film formation of the gas sensing layer of the first embodiment. According to the production method of the present embodiment, lanthanum dioxycarbonate composed of substantially 100% hexagonal crystal structure can also be produced by production of the powder of lanthanum dioxycarbonate composed of monoclinic crystal structure or lanthanum dioxycarbonate containing both hexagonal and monoclinic crystal structure and heat-treating the powder under the conditions shown as the aging condition in the first embodiment.

Fourth Embodiment: Production Method of Monoclinic Samarium Dioxycarbonate

In production of the rare earth metal oxycarbonate shown in the second embodiment, when the rare earth metal is samarium (Sm) and the starting material is samarium acetate hydrate represented by $Sm[CH_3COO]_3 \cdot nH_2O$ or samarium oxalate hydrate represented by $Sm_2[C_2O_4]_3 \cdot nH_2O$, monoclinic samarium dioxycarbonate can be selectively produced under specific heating conditions. Specifically, monoclinic samarium dioxycarbonate can be obtained by setting temperature and time to specific values while the starting material and the production conditions are within the scope of the second embodiment.

Monoclinic samarium dioxycarbonate represented by $Sm_2O_2CO_3$ can be produced by a step of heating samarium acetate hydrate represented by $Sm[CH_3COO]_3 \cdot nH_2O$ or samarium oxalate hydrate represented by $Sm_2[C_2O_4]_3 \cdot nH_2O$ in the air, for example in a gas atmosphere containing 350 to 500 ppm of carbon dioxide, at a heating temperature of 425 to 475° C. for 2 to 80 hours.

The monoclinic samarium dioxycarbonate produced by the present embodiment has excellent stability and gas sensitivity, and can be used as a sensing layer of a $CO_2$ gas sensor. Furthermore, this monoclinic samarium dioxycarbonate is advantageous since it provides $CO_2$ gas sensitivity even without being subjected to aging under the aging conditions shown in the first embodiment, and since it maintains high gas sensitivity even when being subjected to aging.

EXAMPLE

Hereinafter, the present invention will be described in more detail with reference to the Examples of the present invention. However, the present invention is not limited to the Examples below.

(1) Production of Lanthanum Dioxycarbonate

For the purpose of producing a rare earth oxycarbonate in which the rare earth element is lanthanum (La), two synthetic pathways using different starting materials were investigated. FIG. 3 shows the synthetic pathway using a hydroxide as a starting material (pathway 1), and the synthetic pathway using an oxalate hydrate as a starting material (pathway 2). A solid powder of commercially available $La(OH)_3$ (Sigma-Aldrich Co. LLC.) was used as a starting material in pathway 1, and a solid powder of commercially available $La_2[C_2O_4]_3 \cdot nH_2O$ (Sigma-Aldrich Co. LLC.) was used as a starting material in pathway 2. The powder of the starting material was put in an alumina container, and heated using a heating furnace. During heating, air was continuously supplied to the heating furnace by a pump. The heating time and the heating temperature are shown in Table 1 for pathway 1 and in Table 2 for pathway 2.

TABLE 1

| Temperature | Time (hour) | | |
|---|---|---|---|
| (° C.) | 6 | 18 | 72 |
| 550 | — | — | — |
| 500 | — | $La_2O_3$ | — |
| 450 | $La_2O_3$ | #1: h | — |
|  |  | #2: $La_2O_3$ |  |

TABLE 2

| Temperature | Time (hour) | | |
|---|---|---|---|
| (° C.) | 6 | 18 | 72 |
| 550 | (a) m | (b) m + h | (c) h |
| 500 | (d) m + c | (e) m | (f) h |
| 450 | (g) m + c | (h) m + c | (i) m |

The material generated by each heat treatment was measured using an X-ray diffractometer. The material obtained by each heating time and each heating temperature is shown in Table 1 and Table 2. In Table 1 and Table 2, "m" representing a product is monoclinic lanthanum dioxycarbonate, "h" is hexagonal lanthanum dioxycarbonate, and "c" is carbon. The "m+h" shows the state in which both monoclinic and hexagonal crystal structures are contained, and "m+c" shows the state in which both monoclinic crystal structure and carbon are contained.

From these results, oxide $La_2O_3$ tended to be generated in pathway 1, while lanthanum dioxycarbonates were obtained under all conditions in pathway 2. However, the crystal structures differed and carbon residues were generated in some conditions. In the case of heating at 450° C. in pathway 1, hexagonal lanthanum dioxycarbonate was generated in the first production shown in #1 of Table 1, and $La_2O_3$ was generated in the second production in #2 of Table 2. Generating of hexagonal lanthanum dioxycarbonate could not be reproduced.

Each product in Table 1 and Table 2 was observed by a scanning microscope (results not shown). When an oxalate was used as a starting material, formation of sponge-like micropores suitable for a gas sensor could be clearly observed. It is thought that when the starting material was transformed into the oxycarbonate by heat treatment, the chemical reaction represented by the formula below occurred and finally $CO_2$ and $H_2O$ were generated, and thus, the pores from which the gases escaped formed sponge-like micropores.

$$2La_2[C_2O_4]_3 \cdot nH_2O + 3O_2 \rightarrow 2La_2O_2CO_3 + 10CO_2 + nH_2O \quad \text{[Chemical Formula 1]}$$

On the other hand, in the hexagonal lanthanum dioxycarbonate obtained using a hydroxide as a starting material, sponge-like micropores were not observed.

(2) Production of Gas Sensor Structure Having Sensing Layer Containing Lanthanum Dioxycarbonate The gas sensor structure shown in FIG. 1 was produced. An alumina substrate having a thickness of 900 μm was used as the insulating substrate 3, and a Pt heater having a thickness of 5 μm was provided on one major surface of the insulating substrate 3. Comb teeth-shaped Pt film having a thickness of 5 μm was used for the electrodes 2, and the gap between the teeth of the comb was 10 μm. The solid powder of the lanthanum dioxycarbonate produced in (1) and propane-1,2-diol were mixed by a vibration mill at 30 Hz for 30 minutes, and then the obtained paste was screen-printed on the insulating substrate 3 provided with the Pt electrodes 2, and thus, the gas sensing layer 1 was produced. The thickness of the gas sensing layer 1 as measured from the surface of the insulating substrate 3 was 50 μm. The gas sensor having the gas sensing layer 1 was produced, wherein the gas sensing layer 1 was film-formed using each of hexagonal lanthanum dioxycarbonate shown in #1 of Table 1 and the products (c), (e), (f), (h) and (i) shown in Table 2.

The Pt heater was connected to a DC power source (not shown), and thus, the sensor was enabled to be heated to a temperature of 250° C., 300° C., or 350° C. The gas sensing layer 1 was connected to an electrical resistance measurement apparatus (not shown) via the electrode 2 to provide a configuration which enabled measurement of DC resistance of the gas sensing layer at 10 second intervals.

(3) Durability Test and Comparison of Properties

As accelerated durability tests for evaluating long term stability of the produced sensor structure, aging was conducted under the specified conditions and, $CO_2$ sensitivity properties before and after the test were evaluated. In the sensor structure to be measured, the products shown in #1 of Table 1 and (e), (f) and (h) shown in Table 2 were used as the materials for the gas sensing layer 1. The durability test was conducted by operating the heating layer for 72 hours at 350° C. under the conditions of relative humidity of 80% at 20° C. and carbon dioxide concentration of 300 ppm. These conditions for the durability test are almost the same as the aging condition for stabilizing of initial properties of the gas sensor in the present invention. The properties of the gas sensor were evaluated using DC resistance (Rs) of the gas sensing layer. The relationship between the DC resistance before the durability test and the carbon dioxide concentration is shown in FIG. 4A, and the relationship after the durability test is shown in FIG. 4B. The results of FIGS. 4A and 4B show that products #1 and (f) composed of hexagonal lanthanum dioxycarbonate were stable after the durability test with the $CO_2$ sensitivity property (DC resistance) was unchanging, whereas the resistance of products (h) and (e) significantly increased. As the result of investigations by X-ray crystal diffraction, the gas sensing layers containing products (h), (i) and (e) that were constituted of monoclinic lanthanum dioxycarbonate before the durability test became the state in which both monoclinic and hexagonal crystal structures were contained after the durability test. On the other hand, the gas sensing layers of #1 and (f) constituted of hexagonal lanthanum dioxycarbonate before the durability test exhibited no changes after the durability test.

Figure 5A:
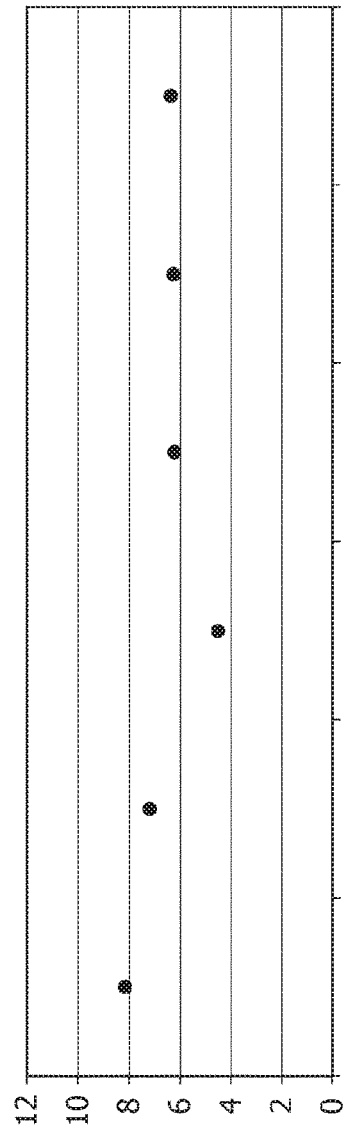
FIG. 5A to 5C show the results of investigating gas sensor properties of 6 types of sensors each comprising the gas sensing layer comprising lanthanum dioxycarbonate produced by different methods.
Figure 5B:
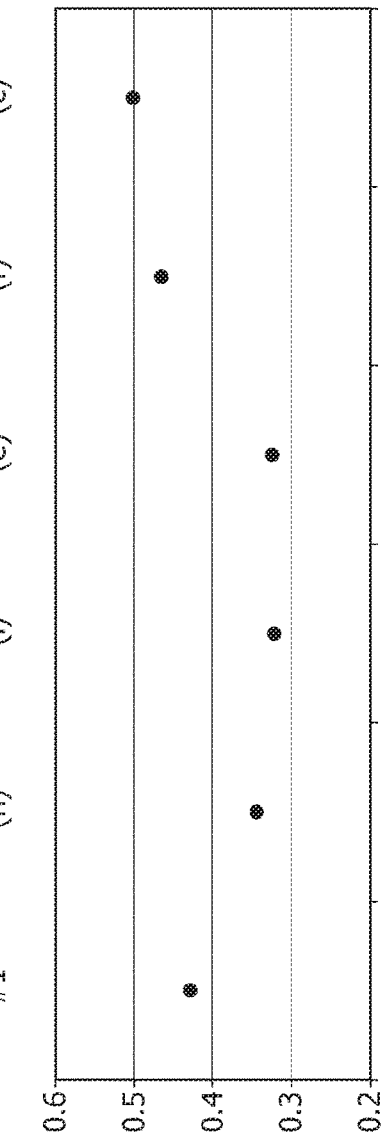
Figure 5C:
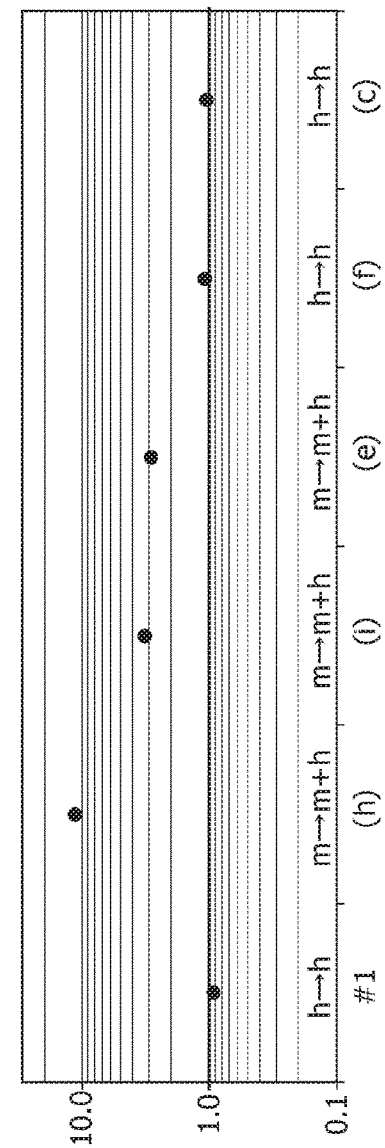

Next, the $CO_2$ gas sensor signal ($R_g/R_0$), sensitivity ($\alpha$), change of sensor resistance value (after durability test/initial stage) were evaluated for 6 types of gas sensing layer materials which were produced by different methods. The results are shown in FIG. 5A to 5C. FIG. 5A is a graph showing the $CO_2$ gas sensor signal of initial stage. $CO_2$ gas sensor signal $R_g/R_0$ represents (DC resistance value of the sensor when the sensor was driven at a specified $CO_2$ concentration)/(DC resistance value of the sensor when the sensor was driven at $CO_2$ concentration of 0 ppm). In FIG. 5A, $R_{CO2\ 1000\ ppm}/R_0$ at a specified $CO_2$ concentration of 1000 ppm was measured in relative humidity of 50% at 20° C. The operating temperature was 300° C. In FIG. 5B, sensitivity ($\alpha$) in the initial stage (before aging) is an indicator defined as $R_g/R_0=A\times[CO_2\ concentration]^\alpha$, wherein A and $\alpha$ are constant numbers. FIG. 5C shows change in DC resistance value of the sensor as measured at a $CO_2$ concentration of 1000 ppm, which shows the change after durability test/initial stage described in the above (3), i.e., stability of the resistance value. In FIG. 5A to 5C, the horizontal axis represents each product produced in Example (2). In FIG. 5C, the crystal structures before and after aging are shown as (structure before aging→structure after aging). In the figure, "m" indicates monoclinic crystal structure, and "h" indicated hexagonal crystal structure. From these results, it is considered that hexagonal lanthanum dioxycarbonate is superior to monoclinic lanthanum dioxycarbonate in terms of the sensitivity and change of sensor resistance value (stability). No significant difference was observed for the sensor signal.

(4) Aging and Comparison of Structure

Next, the relationship between the aging condition and the change of crystal structure of lanthanum dioxycarbonate constituting the gas sensing layer was investigated. Measurements were conducted using an Operando-XRD apparatus which enabled real time analysis of the structure change and change of sensor resistance value during aging treatment. As a film formation material of the gas sensing layer, product (e) in Table 2 was used. The aging condition for sample #1 of the present experiment was $CO_2$ concentration of 300 ppm, relative humidity of 50% at 20° C. and operating temperature of 350° C. from the start until 56 hours is reached, and after 56 hours passed, the condition was $CO_2$ concentration of 1000 ppm, relative humidity of 0% at 20° C. and operating temperature of 350° C. The aging condition for sample #2 of the present experiment was $CO_2$ concentration of 3000 ppm, relative humidity of 80% at 20° C., and operating temperature of 350° C. without changing the aging condition in the process of aging. The results are shown in FIG. 6.

Figure 6A:
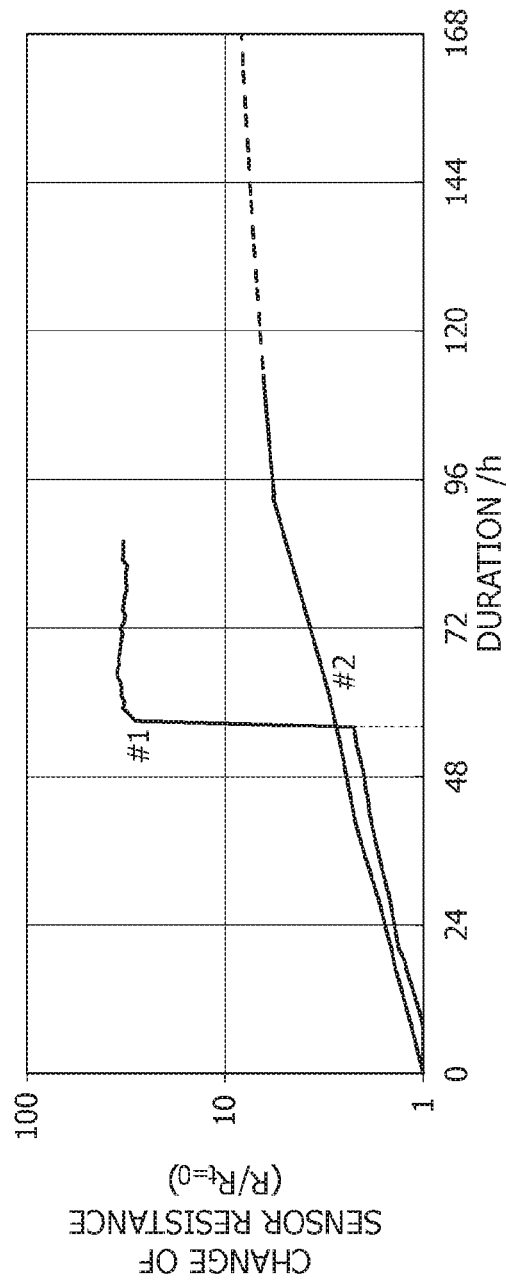
FIG. 6A to 6B are graphs showing relationships between aging conditions and properties of the gas sensing layer.
Figure 6B:
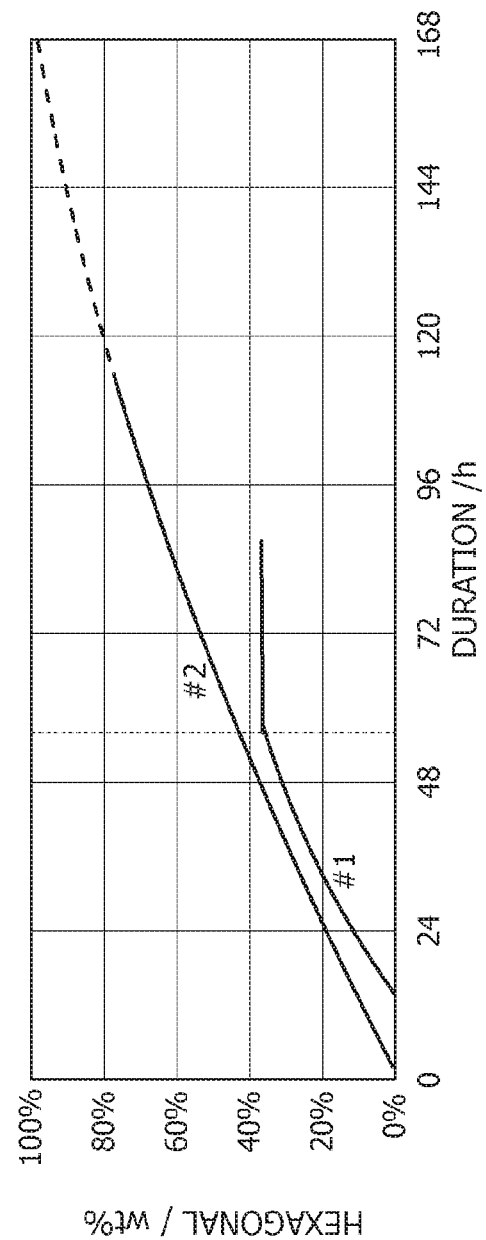

In both FIGS. 6A and 6B, the horizontal axis is aging treatment time, the vertical axis in FIG. 6A represents the sensor resistance value and the vertical axis in FIG. 6B represents the mass ratio of hexagonal lanthanum dioxycarbonate (mass %) relative to the total mass of lanthanum dioxycarbonate. From FIGS. 6A and 6B, it was found that monoclinic crystal structure can be transformed into hexagonal crystal structure by aging. Therefore, stabilizing initial properties of the gas sensor can be contemplated by conducting aging of the gas sensing layer. Furthermore, as for the aging conditions, when both humidity and $CO_2$ were provided, the structure of lanthanum dioxycarbonate and the sensor resistance value were both changed, while no change was observed in the case of providing only $CO_2$.

(5) Dual Sensing of Humidity and $CO_2$ Concentration

Figure 7:
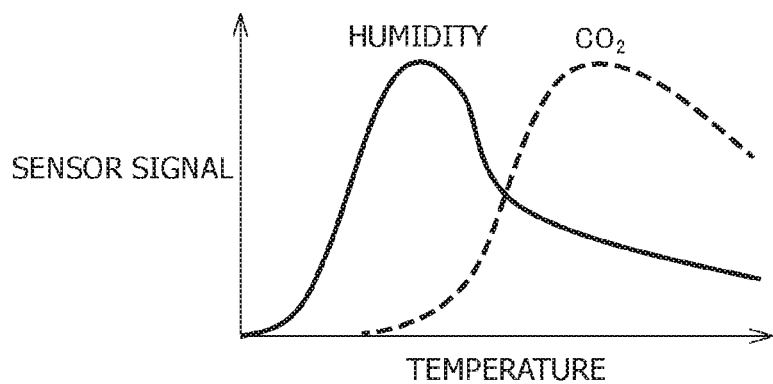
FIG. 7 is a graph schematically showing the sensor signal property change of the rare earth metal dioxycarbonate with respect to temperature, which enables dual sensing of humidity and $CO_2$ concentration.

It was found that the sensor resistance value changed not only by $CO_2$ concentration but also by humidity in this material system. However, when the sensor properties were not changed, it is necessary to prepare another humidity sensor to correct humidity in practical use. As shown in FIG. 7, it has been found that if there are temperatures at which the sensor signal to humidity is high and temperatures at which the sensor signal to $CO_2$ is high, there is the possibility of detecting humidity and $CO_2$ concentration by the same sensor at the same time by detecting humidity and $CO_2$ at the two temperature point. The following experiment was conducted with regard to such property.

Figure 8:
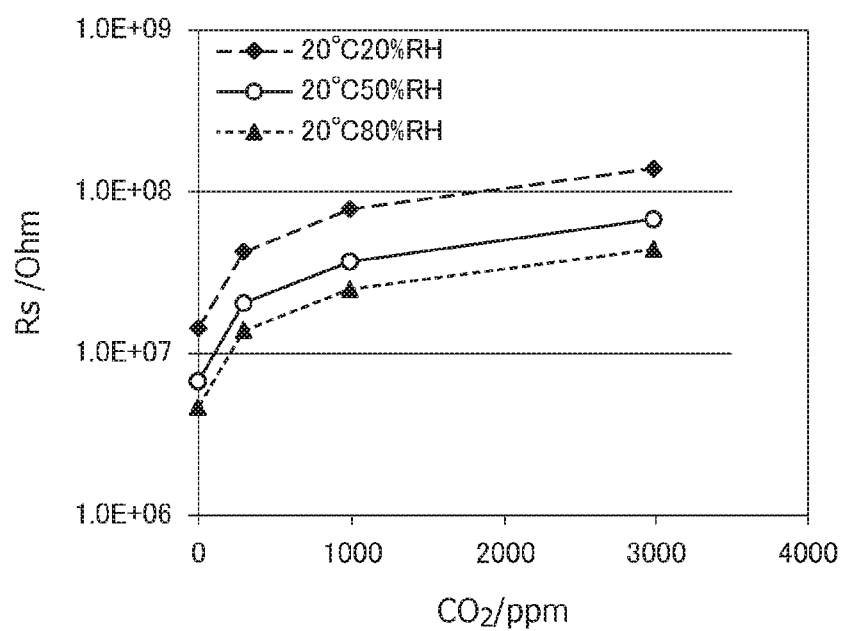
FIG. 8 is a graph showing results of investigating relationships between $CO_2$ concentration and DC resistance values of the sensor comprising a gas sensing layer composed of lanthanum dioxycarbonate while changing the relative humidity from 20% RH to 80% RH at 20° C.
Figure 9:
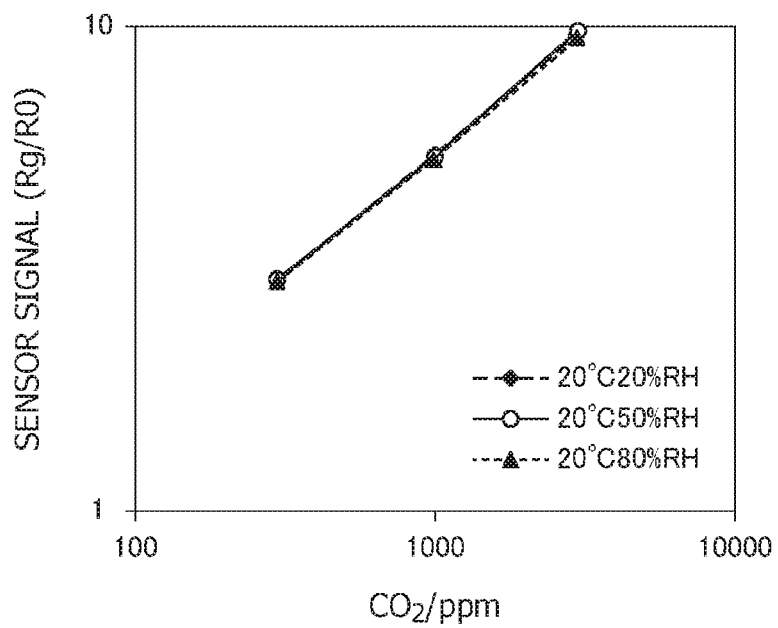
FIG. 9 is a graph showing results of investigating relationships between the $CO_2$ concentration and sensor signal of the sensor comprising a gas sensing layer composed of lanthanum dioxycarbonate while changing the relative humidity from 20% RH to 80% RH at 20° C.

In the present experiment, the sensor structure shown in FIG. 1 was used, in which the gas sensing layer was film-formed using the product (c) in Table 2 and was subjected to aging so that the gas sensing layer contained 100% hexagonal lanthanum dioxycarbonate. The relationship between $CO_2$ concentration and the DC resistance value of the sensor was investigated by varying the relative humidity at 20° C. from 20% RH to 80% RH. The operating temperature of the sensor was 300° C. The results are shown in FIG. 8. The relationship between $CO_2$ concentration and the sensor signal was investigated in the similar way. The operating temperature of the sensor was 300° C. The results are shown in FIG. 9. As can be seen from FIG. 8 and FIG. 9, the curves of the DC resistance value of the sensor vs. $CO_2$ concentration shift depending on humidity but the inclination of the curves do not change, and thus, it is considered that the relationship between the sensor signal and $CO_2$ concentration hardly depends on humidity.

Figure 10:
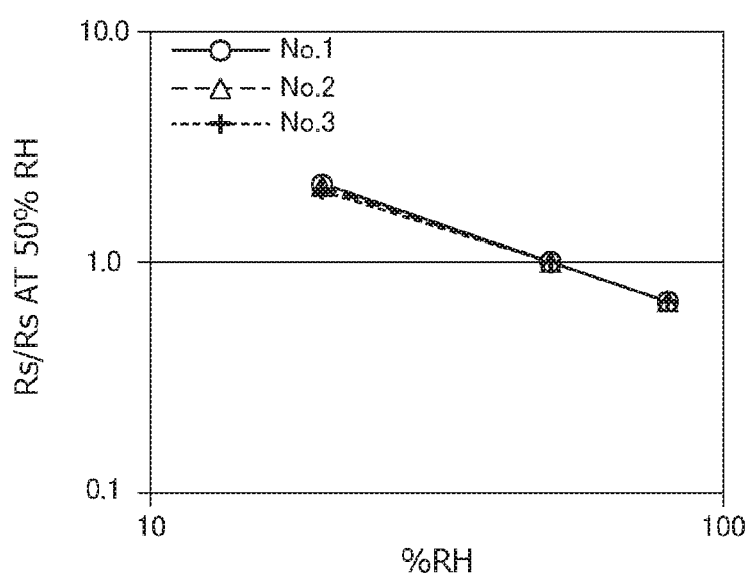
FIG. 10 is a graph showing results of measuring humidity dependence of sensor resistance values (normalized values based on the value at 50% RH) of the 3 sensors each comprising a gas sensing layer composed of lanthanum dioxycarbonate while changing the relative humidity from 20% RH to 80% RH at 20° C. in an atmosphere containing 1000 ppm of $CO_2$.

The humidity dependence of the sensor resistance value in 1000 ppm of $CO_2$ was measured in the case of varying the relative humidity at 20° C. from 20% RH to 80% RH. The sensor resistance values were normalized values based on the value at 50% RH, and were measured for 3 sensors. The results are shown in FIG. 10. In the graph, 300° C. is shown as the operating temperature of the sensor. The humidity dependence was large, but variation between individual sensors was hardly observed. The sensor resistance value and humidity were in a linear relationship in a logarithmic graph, which indicated large dependence wherein increase by one digit of the humidity resulted in decrease by one digit of the sensor resistance value. The variation between individual sensors was hardly observed and linearity was high, and thus, it was found that correction by another humidity sensor can be sufficiently possible.

(6) Production of Lanthanum Dioxycarbonate, Neodymium Dioxycarbonate, and Samarium Dioxycarbonate Rare earth oxycarbonates in which the rare earth element was lanthanum (La), neodymium (Nd), and samarium (Sm) were produced. Solid powders of $La_2[C_2O_4]_3 \cdot nH_2O$ (lanthanum oxalate, oxalic acid salt, produced by Sigma-Aldrich Co. LLC.), $Nd[CH_3COO]_3 \cdot nH_2O$ (neodymium acetate, acetic acid salt, produced by Sigma-Aldrich Co. LLC.) and $Sm[CH_3COO]_3 \cdot nH_2O$ (samarium acetate, acetic acid salt, produced by Sigma-Aldrich Co. LLC.) were used as starting materials. The powder of the starting material was put in an alumina container and was heated using a heating furnace. During heating, air was continuously supplied to the heating furnace by a pump. The heating time and the heating temperature were as shown in Table 3. The obtained products were subjected to crystal structure analysis by XRD. The oxycarbonate of La was stable in all the conditions below, the oxycarbonates of Nd and Sm were stable up to 500° C., for 18 h and up to 450° C., for 18 h respectively.

TABLE 3

| Rare earth element | La | Nd | Sm |
|---|---|---|---|
| Starting material | ox | ac | ac |
| 550° C. 72 h | h | $Nd_2O_3$ | $Sm_2O_3$ |
| 550° C. 18 h | m + h | $Nd_2O_3$ | — |
| 550° C. 06 h | m | — | — |
| 500° C. 72 h | h | $Nd_2O_3$ | — |
| 500° C. 18 h | m | m | $Sm_2O_3$ |
| 500° C. 06 h | m | — | — |
| 450° C. 72 h | m | — | $Sm_2O_3$ |
| 450° C. 18 h | m | m | m |
| 450° C. 06 h | m | — | — |
| 450° C. 02 h | m | m | m |

In the table, "m" indicates monoclinic rare earth oxycarbonate, "h" indicates hexagonal rare earth oxycarbonate, "ox" indicates oxalate hydrate, and "ac" indicates acetate hydrate. The "-" means that no heating experiment was conducted in the corresponding conditions.

(7) Production of Gas Sensors Having Sensing Layers Each Comprising Lanthanum Dioxycarbonate, Neodymium Dioxycarbonate and Samarium Dioxycarbonate, Respectively The gas sensor structure shown in FIG. 1 was produced in the similar way as in the above Example (2). The specifications of the insulating substrate 3, Pt heater, and electrode 2 were also similar to the above Example (2). The solid powder of lanthanum dioxycarbonate (hexagonal crystal structure) produced in Example (1) and heated at 550° C. for 72 h, and solid powders of neodymium and samarium dioxycarbonate (monoclinic crystal structure) heated at 450° C. for 18 h were used for the gas sensing layer 1. Each of these solid powers and propane-1,2-diol were mixed by a vibration mill at 30 Hz for 30 minutes, then the obtained paste was screen-printed on the insulating substrate 3 provided with the Pt electrode 2, and thus, the gas sensing layer was produced. The thickness of the gas sensing layer 1 as measured from the surface of the insulating substrate 3 was 50 μm.

The Pt heater was connected to a DC power source (not shown), and thus, the sensor was enabled to be heated to a temperature of 250° C., 300° C. or 350° C. The gas sensing layer 1 was connected to a measurement apparatus of electrical resistance (not shown) via the electrode 2 to provide a configuration which enabled measurement of DC resistance of the gas sensing layer at 10 second intervals.

(8) Comparison of Sensor Properties

Figure 11A:
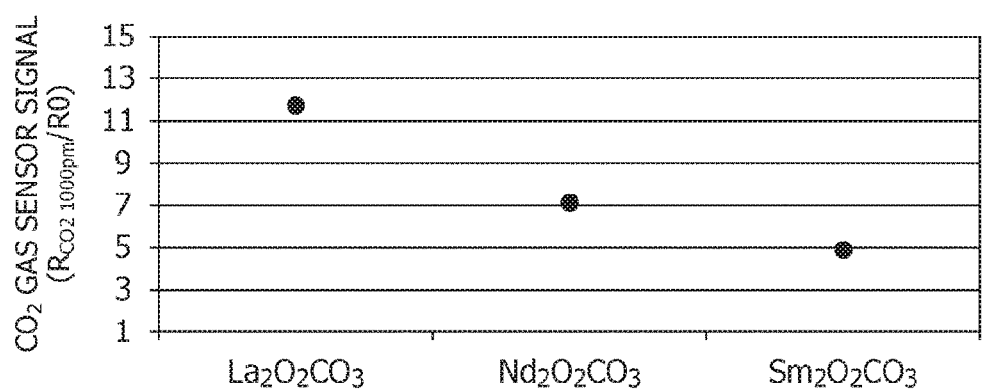
FIG. 11A to 11C show results of investigating gas sensor properties of the 3 types of sensors, each comprising a gas sensing layer composed of hexagonal lanthanum dioxycarbonate, monoclinic neodymium dioxycarbonate, monoclinic samarium dioxycarbonate respectively under the condition of 20° C., relative humidity of 50% RH and operating temperature of 300° C.
Figure 11B:
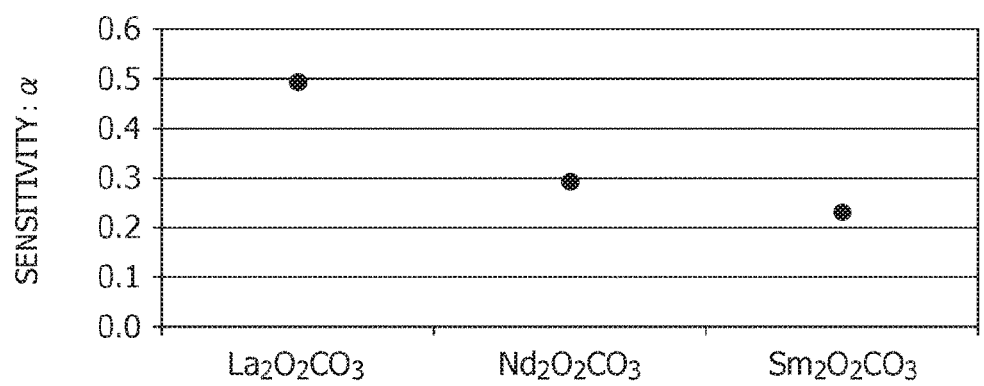

The $CO_2$ gas sensor signal $R_{CO2\ 1000\ ppm}/R_0$ of the produced sensor was obtained from the DC resistance value as measured under the conditions of $CO_2$ concentration of 1000 ppm, 20° C., relative humidity of 50% RH, and operating temperature of 300° C. $R_{CO2\ 1000\ ppm}/R_0$ is defined similarly to the above Example (3). Similarly, the sensitivity α was obtained. The value of the sensitivity α is also defined similarly to the above Example (3). FIG. 11A and FIG. 11B show the results of comparing the $CO_2$ gas sensor signal and sensitivity α of the sensors each having the sensing layer constituted of rare earth oxycarbonate ($La_2O_2CO_3$, $Nd_2O_2CO_3$, $Sm_2O_2CO_3$). Both $CO_2$ gas sensor signal and sensitivity α were higher in the order of $La_2O_2CO_3$ (hexagonal crystal structure)>$Nd_2O_2CO_3$ (monoclinic crystal structure)>$Sm_2O_2CO_3$ (monoclinic crystal structure).

Figure 11C:
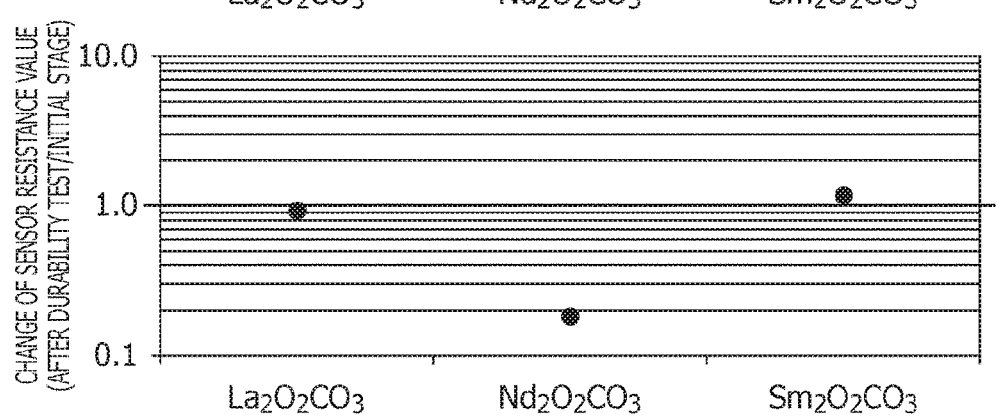

In order to evaluate the long term stability of the sensors, changes of the DC resistance values as measured under the conditions of $CO_2$ concentration of 1000 ppm, 20° C., relative humidity of 50% RH and operating temperature of 300° C. were measured before and after electrifying the sensor for 3 days in an atmosphere of high $CO_2$ concentration and high humidity (3000 ppm, 20° C., relative humidity 80% RH) at an operating temperature of 350° C. which is higher than standard temperature of 300° C. The results are shown in FIG. 11C. It can be seen that the sensor resistance value was significantly reduced only in the case of neodymium dioxycarbonate. The reason is that neodymium dioxycarbonate was transformed into neodymium oxide. Both the sensor signal and sensitivity were stable in the case of lanthanum dioxycarbonate and samarium dioxycarbonate.

(9) Selectivity and $CO_2$ Sensitivity Over Range Up to High Concentration

Figure 12A:
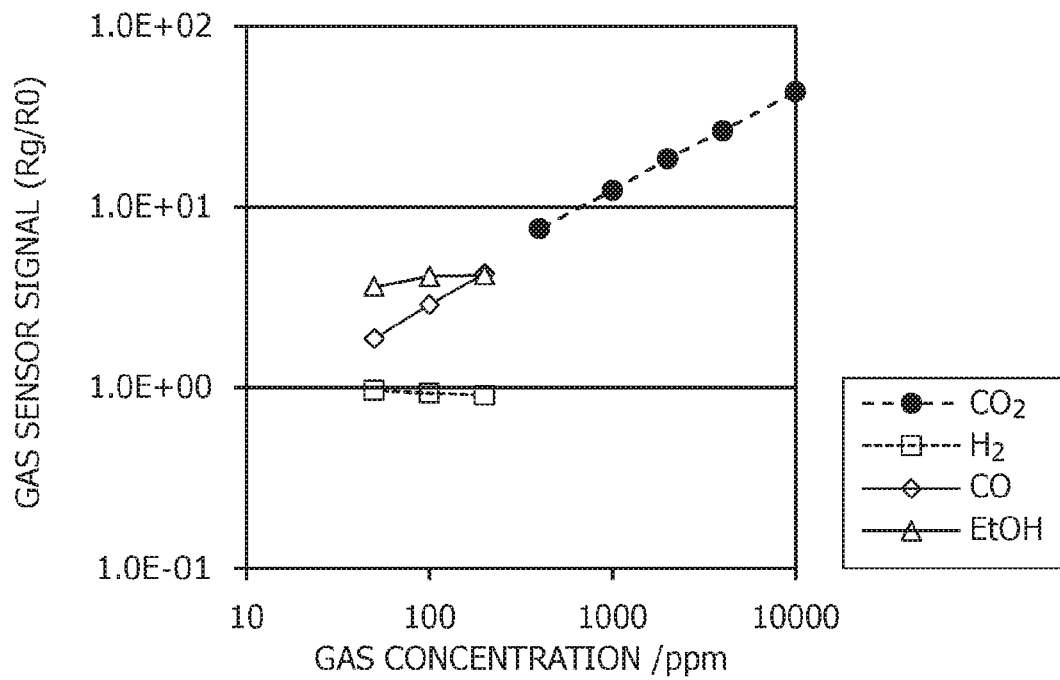
FIG. 12A to 12B are graphs showing results of investigating relationships between the gas concentrations and sensor signal ($R_g/R_0$) to four kinds of gases $CO_2$, $H_2$, CO and ethanol for the sensors each comprising a gas sensing layer under the condition of 20° C., relative humidity of 50% RH, and operating temperature of 300° C.
Figure 12B:
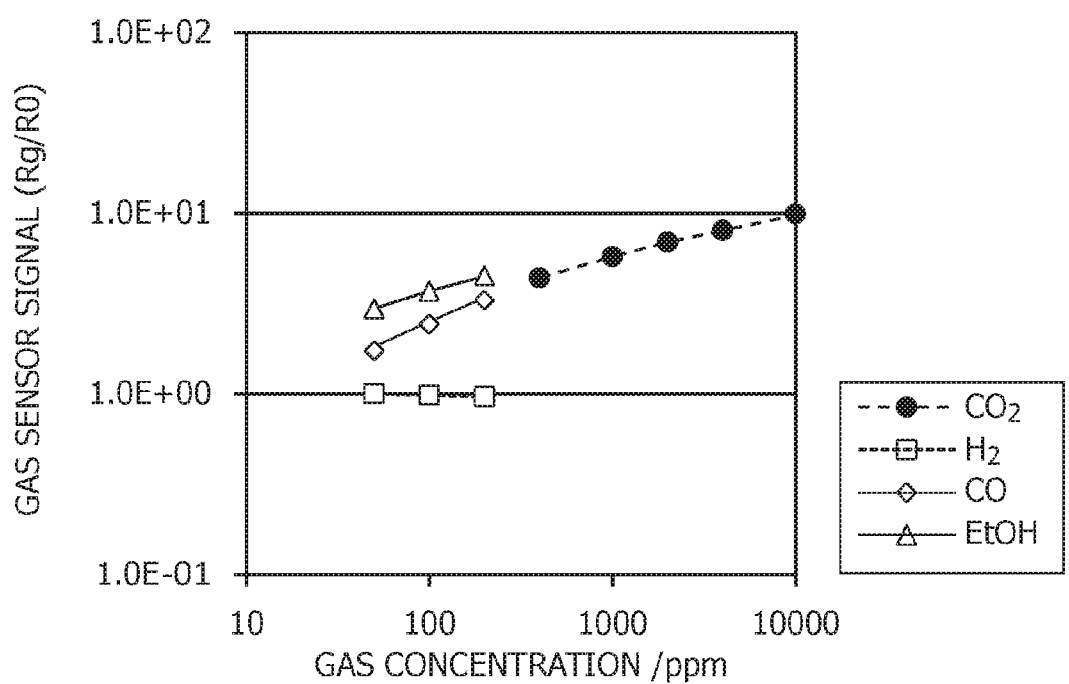

The gas selectivity and $CO_2$ sensitivity over the range up to high concentration were evaluated for the sensors in which lanthanum dioxycarbonate and samarium dioxycarbonate having excellent durability were respectively used for the sensing layer. The change of the gas sensor signal to each gas concentration of four kinds of gases, $CO_2$, $H_2$, CO, and ethanol (EtOH) is shown in FIG. 12A for the sensor having the sensing layer of lanthanum dioxycarbonate, and in FIG. 12B for the sensor having the sensing layer of samarium dioxycarbonate. The gas sensor signal $R_g/R_0$ represents (DC resistance value of the sensor when the sensor is driven at a specified gas concentration)/(DC resistance value of the sensor when the sensor is driven in an atmosphere not comprising $CO_2$). The measurements were conducted under the conditions of 20° C., relative humidity of 50% RH, and operating temperature of 300° C. For both sensors, the $CO_2$ sensor signal was linear over the range up to 10,000 ppm in double logarithmic graphs and the sensitivity barely changed.

Figure 13A:
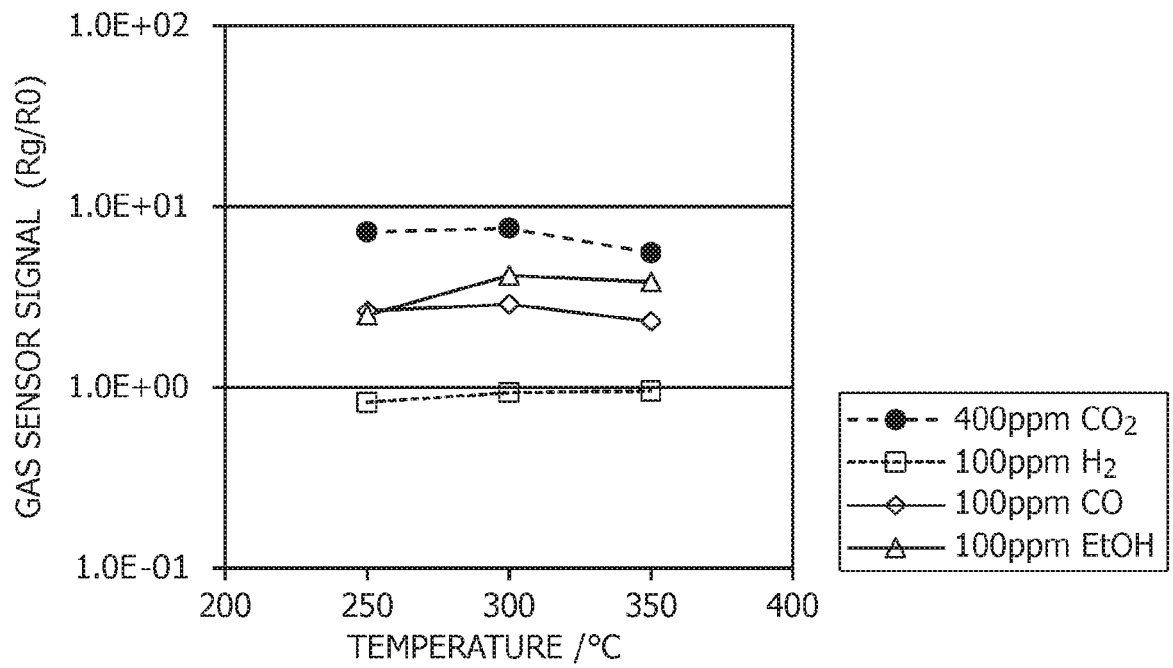
FIG. 13A to 13B are graphs showing results of investigating relationship between the sensor operating temperatures and sensor signal ($R_g/R_0$) to four kinds of gases $CO_2$, $H_2$, CO and ethanol for the sensors each comprising a gas sensing layer under the condition of 20° C. and relative humidity of 50% RH.
Figure 13B:
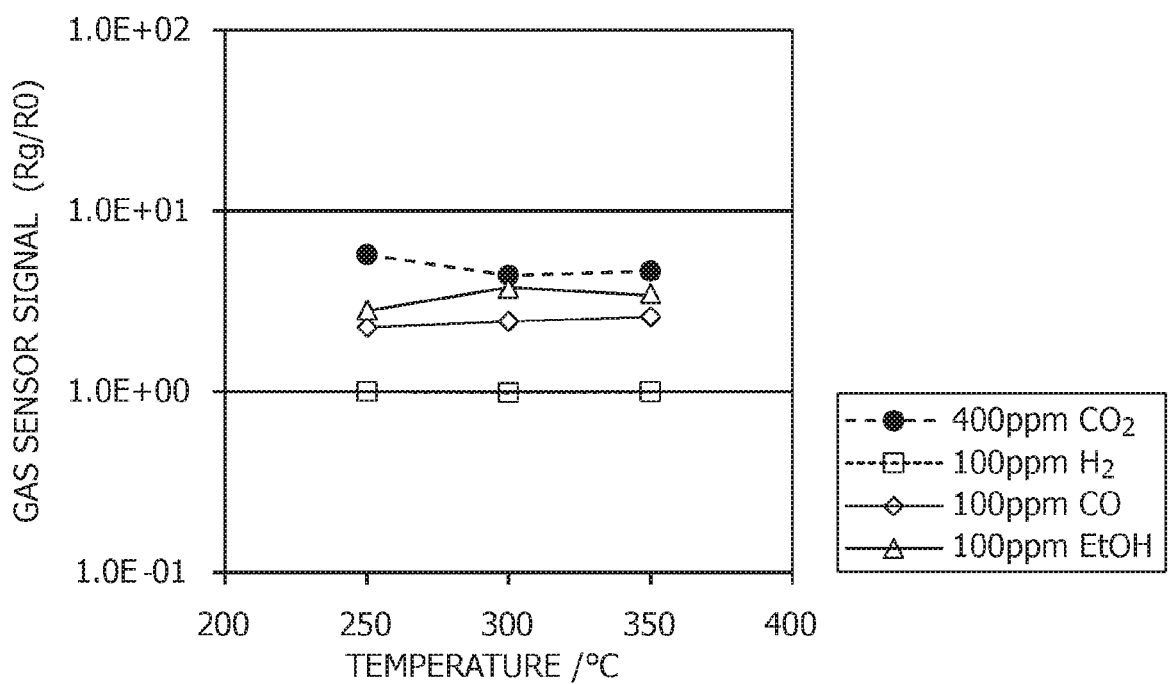

Next, temperature dependence of the sensor signal to four kinds of gases $CO_2$, $H_2$, CO, ethanol (EtOH) of the specified concentration was evaluated. FIG. 13A shows the results for the sensor having the sensing layer of lanthanum dioxycarbonate, and FIG. 13B shows the results for the sensor having the sensing layer of samarium dioxycarbonate. The $CO_2$ gas concentration of 400 ppm was the lowest concentration within the range estimated for the current atmospheric environment level. On the other hand, hydrogen, CO, and ethanol gas concentrations of 100 ppm were highest concentrations within the range estimated very severely. The gas sensor signal $R_g/R_0$ is defined similarly to the above, and the measurements were conducted under the conditions of 20° C., relative humidity of 50% RH, and operating temperature of 300° C. For all sensors, the $CO_2$ sensor signal was higher than the sensor signals to other various gases. Among various gases, sensor signal to ethanol, CO were high, in this order, and there was almost no sensor signal to hydrogen. It was shown that the properties of $La_2O_2CO_3$ were particularly excellent with regard to both selectivity and $CO_2$ sensitivity.

INDUSTRIAL APPLICABILITY

The gas sensor according to the present invention is useful as a MEMS solid gas sensor that has low power consumption in consideration of being driven by a battery.

REFERENCE SYMBOL LIST

1 Gas sensing layer
2 Electrode
3 Insulating substrate
4 Heating layer
11 Gas sensing layer
12a Electrode
12b Bonding layer
13 Insulating substrate
14 Heating layer
15 Thermally insulating support layer
16 Si substrate

The invention claimed is:

1. A carbon dioxide gas sensor comprising:
an insulating substrate; and
a gas sensing layer formed on one major surface of the insulating substrate via electrodes, wherein the gas sensing layer comprises monoclinic samarium dioxycarbonate.

2. A method for production of a carbon dioxide gas sensor, comprising:
forming monoclinic samarium dioxycarbonate by heating samarium acetate hydrate or samarium oxalate hydrate; and
applying the formed monoclinic samarium dioxycarbonate on one major surface of an insulating substrate via electrodes to form a gas sensing layer of a sensor structure.

3. The method of claim 2, wherein the heating comprises:
heating the samarium acetate hydrate represented by $Sm[CH_3COO]_3 \cdot nH_2O$ or the samarium oxalate hydrate represented by $Sm_2[C_2O_4]_3 \cdot nH_2O$ in a gas atmosphere containing 350 ppm to 500 ppm of carbon dioxide, at a heating temperature of 425° C. to 475° C. for 2 hours to 80 hours.

* * * * *